United States Patent
Ackerman et al.

(10) Patent No.: US 6,723,053 B2
(45) Date of Patent: Apr. 20, 2004

(54) ESOPHAGEAL BALLOON CATHETER DEVICE

(75) Inventors: Bernard Ackerman, Metuchen, NJ (US); Robert M. Landis, Mountainside, NJ (US)

(73) Assignee: CooperSurgical, Inc., Trumbull, CT (US)

( * ) Notice: Subject to any disclaimer, the term of this patent is extended or adjusted under 35 U.S.C. 154(b) by 0 days.

(21) Appl. No.: 09/808,080

(22) Filed: Mar. 14, 2001

(65) Prior Publication Data

US 2002/0133081 A1 Sep. 19, 2002

(51) Int. Cl.[7] .................................................. A61B 5/02
(52) U.S. Cl. ........................ 600/486; 600/485; 600/561; 600/585
(58) Field of Search ................ 600/433–435, 600/466, 470, 481, 485, 585, 486, 561; 604/96.01, 264, 508, 523, 915, 920, 921

(56) References Cited

U.S. PATENT DOCUMENTS

| | | | |
|---|---|---|---|
| 3,480,003 A | | 11/1969 | Crites |
| 3,710,781 A | * | 1/1973 | Hutchins, IV et al. ...... 600/488 |
| 4,214,593 A | | 7/1980 | Imbruce et al. |
| 4,981,470 A | * | 1/1991 | Bombeck, IV .............. 600/350 |
| 5,117,828 A | | 6/1992 | Metzger et al. |
| 5,419,340 A | | 5/1995 | Stevens |
| 5,551,439 A | | 9/1996 | Hickey |
| 5,716,318 A | * | 2/1998 | Manning ..................... 600/16 |
| 5,836,892 A | | 11/1998 | Lorenzo |
| 5,836,895 A | | 11/1998 | Ramsey, III |
| 5,836,951 A | * | 11/1998 | Rosenbluth et al. ........ 606/108 |
| 5,921,935 A | * | 7/1999 | Hickey ........................ 600/485 |
| 6,259,938 B1 | * | 7/2001 | Zarychta et al. ............ 600/380 |
| 6,322,514 B1 | * | 11/2001 | Holte ........................ 600/481 |
| 6,364,840 B1 | * | 4/2002 | Crowley ..................... 600/463 |

* cited by examiner

Primary Examiner—Robert L. Nasser
Assistant Examiner—Patricia Mallari
(74) Attorney, Agent, or Firm—Lathrop & Gage LC

(57) ABSTRACT

An esophageal catheter device including a catheter with a balloon pressure sensor affixed to an exterior surface of the catheter, and a stylet assembly including a stylet for providing appropriate rigidity to the catheter to aid insertion in the esophagus and a port for removably mounting a pressure transducer.

6 Claims, 2 Drawing Sheets

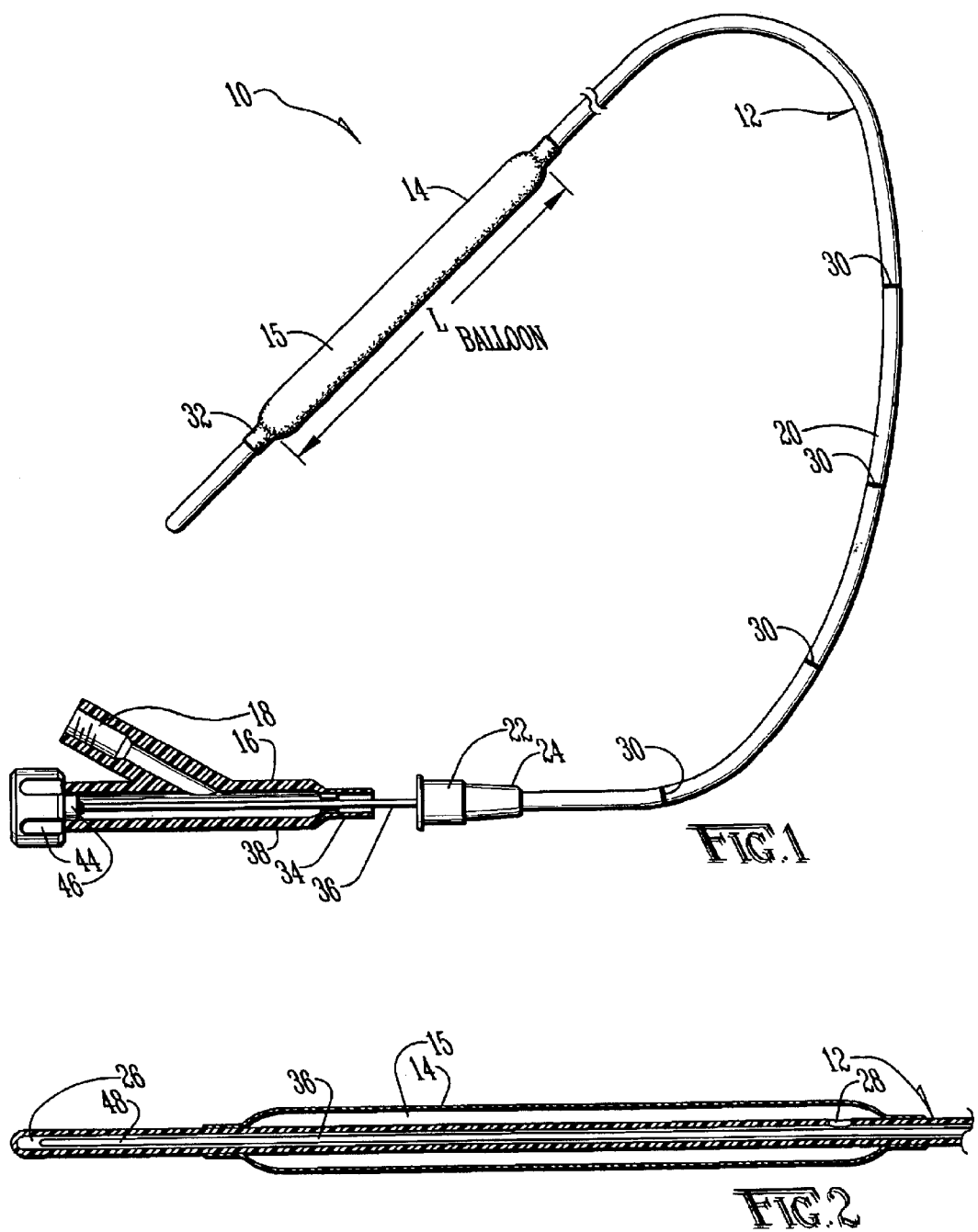

ESOPHAGEAL BALLOON CATHETER DEVICE

FIELD OF THE INVENTION

The present invention relates to a device that provides a conduit through which intra-thoracic pressures can be monitored and measured. More particularly, the present invention relates to an improved esophageal balloon catheter device that is used to obtain esophageal pressure data for evaluating, treating and diagnosing patients with various respiratory conditions and diseases.

BACKGROUND OF THE INVENTION

Esophageal balloon catheter devices are commonly used as a research or clinical tool in the study of lung mechanics. Specifically, many investigators have utilized esophageal balloons to characterize the mechanical properties of the lung in both health and in disease as well as in determining the work or effort of breathing.

More recently, esophageal balloon catheter devices have been used as part of monitoring systems for diagnosing sleep disorders, the clinical management of ventilator patients, as well as a part of pulmonary function systems in the measurement of lung mechanics.

Typical esophageal balloon catheter devices employ an air-containing balloon sealed over the distal or near distal end of a catheter that transmits balloon pressure to a pressure transducer attached to the proximal end of the catheter. A pressure transducer in this context converts mechanical energy (balloon pressure) into electrical signals and units of measurement. The balloon of the catheter is usually positioned in the lower or middle third of the esophagus to monitor esophageal pressure to determine lung compliance and respiratory effort. As is known; during inhalation the pressure in the esophagus and thorax decreases, while it increases in the viscera below the diaphragm and during exhalation the pressure in the esophagus and thorax increases while it decreases in the viscera below the diaphragm.

The catheter used in these devices is sometimes constructed to be stiff and rigid enough to allow insertion through the nasal passage and down into the esophagus. A serious disadvantage of these devices is that they are uncomfortable to patients being monitored to an extent that the pressure data may be affected as well as the patient's ability to sleep. The catheter used in these devices may also be constructed to be limp and flaccid to provide comfort during overnight esophageal pressure testing. However, the limp and flaccid nature of the catheter makes it virtually impossible to insert it into the esophagus. Accordingly, such a catheter device includes a removable stylet assembly, which consists of a wire that is inserted into the lumen of the catheter at the proximal end thereof to stiffen the catheter so that it can be inserted into the esophagus and the balloon properly positioned therein. Once the balloon of the catheter device is positioned in the esophagus, the stylet assembly needs to be removed so the pressure transducer can be attached to the proximal end of the catheter.

A major disadvantage of these devices is that it is very difficult to position the balloon correctly in the esophagus. There is an advantage in being able to monitor esophageal pressure oscillation while positioning the balloon in the esophagus. This is possible with the stiffer more rigid catheters but not with the more comfortable soft and flaccid catheters. Once the stylet is removed and the pressure transducer attached, it is often discovered that the balloon is not properly positioned in the esophagus. Because the catheter is so soft and flaccid this necessitates removing the pressure transducer and reinserting the stylet into the catheter to stiffen it so that the position of the balloon can be corrected. Unfortunately, reinserting the stylet assembly into the catheter is extremely dangerous as it can puncture the catheter and the esophagus.

Accordingly, there is a need for an improved esophageal balloon catheter device, which is soft and flaccid for comfort and yet allows for monitoring esophageal pressure oscillation to aid proper positioning of the balloon. Such a device would avoid the need for removal of the stylet to attach the pressure transducer and the subsequent risk of reinserting the stylet assembly for balloon repositioning.

SUMMARY OF THE INVENTION

An esophageal catheter device comprises a catheter with a balloon as pressure sensor affixed to an exterior surface of the catheter, and a stylet assembly including a stylet for preventing bending and flexing of the catheter during insertion in the esophagus and a port for removably attaching a pressure transducer.

BRIEF DESCRIPTION OF THE DRAWINGS

The advantages, nature, and various additional features of the invention will appear more fully upon consideration of the illustrative embodiments now to be described in detail in connection with accompanying drawings wherein:

FIG. 1 is an elevational view of an esophageal balloon catheter device according to an exemplary embodiment of the present invention;

FIG. 2 is a sectional view of a balloon air pressure sensor according to an exemplary embodiment of the catheter device of the present invention;

DETAILED DESCRIPTION OF THE INVENTION

Figure 3:
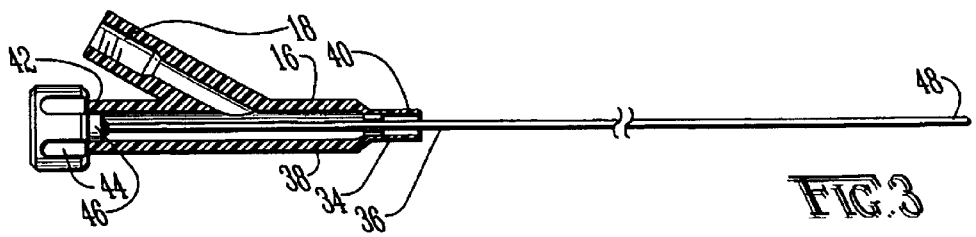
FIG. 3 is a side elevational view of an exemplary stylet transducer coupler assembly according to an exemplary embodiment of the catheter device of the present invention.

Referring to the drawings wherein like reference numerals identify similar or like elements throughout the several views and initially to FIG. 1, there is shown an esophageal balloon catheter device 10 according to an exemplary embodiment of the invention. The catheter device 10 generally comprises a catheter 12, a pressure sensor 14 sealingly affixed to the exterior surface of the catheter 12 in a conventional manner, and a stylet transducer coupler assembly 16 having a transducer port 18 for mounting a pressure transducer which may be used for correctly positioning the pressure sensor 14 of the device in the esophagus. The ability to attach a pressure transducer to the coupler assembly 16 substantially eliminates the need for guess work when placing the pressure sensor 14 in the esophagus.

The catheter 12 typically comprises a 5 french, pliable and soft tubular body 20 which maximizes patient comfort and minimizes effects on normal breathing. The catheter 12 has a length which, in one exemplary embodiment, may be about 87 cm when sized for an adult. A proximal end 24 of the catheter 12 is open, while a distal end 25 of the catheter is closed. A conventional female Luer hub connector 22 or other suitable connector may be provided at the proximal end 24 for permitting a pressure transducer to be easily connected to the catheter 12 as explained further on. As shown in FIG. 2, the catheter 12 defines an inflation lumen 26 that typically extends within the catheter 12 such that it communicates with the interior of the pressure sensor 14 via one or more openings 28 located in a wall portion of the catheter 12 enclosed by the pressure sensor 14.

The catheter 12 is preferably made from a radio-opaque material such as poly(vinyl chloride) or polyurethane. The catheter 12 may be provided with a plurality of depth markings 30, typically in the form of circumferential gradations. The markings 30 are preferably of a type that can be easily seen, therefore, further aiding the user of the catheter device 10 to appropriately position the pressure sensor 14 within the esophagus or other part of the body of the patient.

The pressure sensor 14 preferably comprises an elongated balloon 15 element having a length which is typically about 10 cm and about 3–4 cc in air capacity, although the exact size of the balloon 14 may be selected so that when positioned within the esophagus, it occupies the lower third of the thorax to properly represent intra-thoracic pressure oscillation independent of cardiac oscillation. The balloon 15 may be made from a soft, preferably latex free material such as poly(vinyl chloride) or polyurethane. The distal-most end 32 of the pressure sensor 14 is located about 5 cm from the distal end of the catheter 12 offering a thin lead ahead of the balloon to ease passage through the nasal passages, oral pharynx and esophagus.

Figure 4:
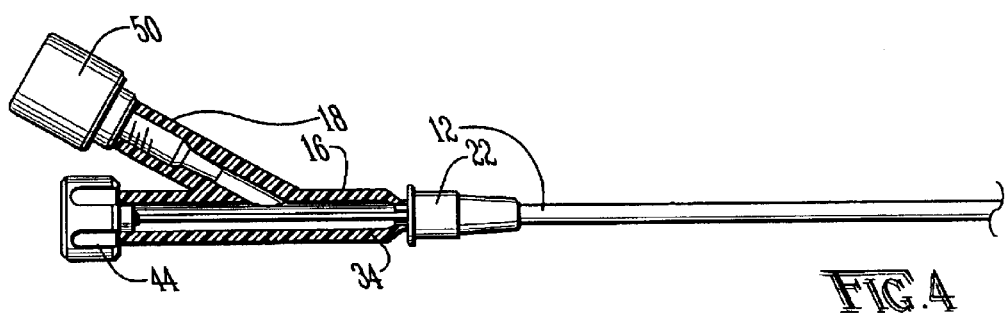
FIG. 4 is a side elevational view showing a pressure transducer mounted to the transducer port of the coupler assembly.
Figure 5:
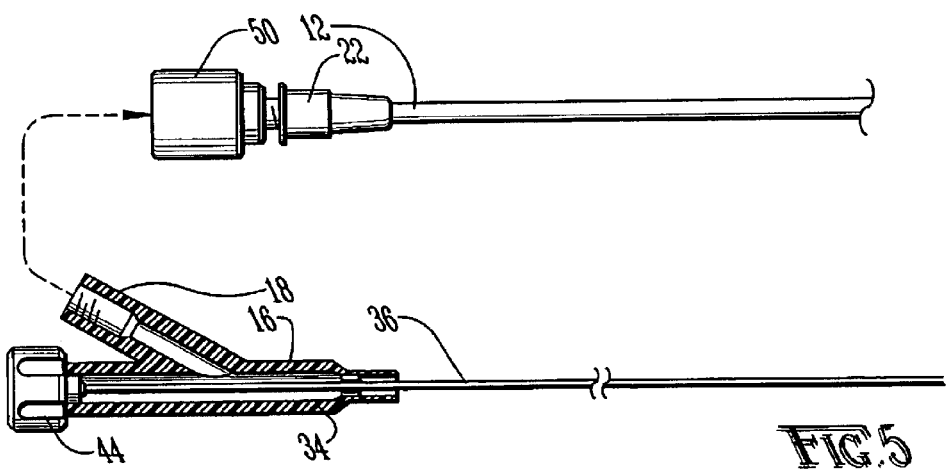
FIG. 5 is a side elevational view showing a pressure transducer mounted to a hub connector of the catheter device.

In operation, the pressure sensor 14 of the catheter device 10 monitors esophageal pressure in the following manner. The balloon 15 is only partially filled with air (about 1 cc) as it rests inside the esophagus. During inhalation intra-thoracic pressure becomes sub-atmospheric (negative). The sub-atmospheric pressure is applied to the walls of the pressure sensor balloon attempting to more fully expand or fill the balloon. During exhalation intra-thoracic pressure becomes positive. The positive pressure is applied to the walls of the pressure sensor balloon attempting to collapse or empty the balloon. The conduit defined by the inflation lumen 26 of the catheter 12 connects the pressure sensor balloon 14 to a transducer attached to the port 18. It is important that the pressure sensor balloon has the correct amount of residual air so slight changes in intra-thoracic pressures are transmitted to the transducer without the distortion of any elastic properties from the balloon wall stretching. The lumen 26 channels air and pressure into the balloon 15 through the one or more openings 28 in the catheter wall that pass directly to the inside of the balloon 15. The pressure in the balloon 15 is transmitted to the proximal end of the lumen 26 which communicates with a pressure transducer 50 via the stylet transducer coupler assembly 16 as shown in FIG. 4 or via the hub connector 22 as shown in FIG. 5. The pressure transducer converts the positive and negative esophageal pressure oscillations (mechanical energy) to electronic signals and units of pressure. The esophageal pressures of the person receiving the catheter device 10 will be reflected by air pressure changes within the balloon 15.

As shown in FIG. 3, the stylet transducer coupler assembly 16 of the catheter device 10 comprises a coupler 34 and a stylet 36. The coupler 34 includes a substantially straight main tube section 38 having distal 40 and proximal ends 42, and the earlier mentioned transducer port tube 18. The distal end 40 of the main tube section 38 is tapered to permit the coupler 34 to be received within the hub connector 22 of the catheter 12 in a friction fit manner. The proximal end 42 of the main tube section 38 is sealed by a cap-like closure 44. The stylet 36 is a wire-like member, the proximal end of which may be permanently affixed to a cylindrical portion 46 of the closure 44 extending into the main tube section 38.

The stylet 36 of the transducer coupler assembly 16 is threaded through the inflation lumen 26 of the catheter 12 (FIG. 2) adding rigidity to the catheter 12, hence aiding the insertion thereof into the esophagus and the positioning of the pressure sensor 14 therein. It is preferred that the distal end 48 of the stylet 36 be blunt (FIG. 2), with a rounded tip, and that the entire stylet be coated with PTFE to aid in removing it from the inflation lumen 26 after the balloon is properly placed.

The transducer port 18 of the stylet coupler assembly 16 is adapted to accept a standard pressure transducer 50 to the coupler assembly 16 so that the transducer 50, in conjunction with the pressure sensor 14, may be used in concert for correctly positioning the pressure sensor in the esophagus. Once the pressure sensor is correctly positioned in the esophagus, the pressure transducer 50 is then removed from the port 18 of the coupler assembly 16. The stylet transducer coupler assembly 16 is withdrawn from the catheter 12. The pressure transducer 50 may then be attached to the connector 22 of the catheter 12 and operated in conjunction with the pressure sensor 14 to monitor esophageal pressure.

While the foregoing invention has been described with reference to the above embodiments, various modifications and changes can be made without departing from the spirit of the invention. Accordingly, all such modifications and changes are considered to be within the scope of the appended claims.

What is claimed is:

1. An esophageal catheter system comprising:
   a catheter including
      an open end, for removably mounting one of a pressure transducer and a stylet assembly,
      a closed end,
      a balloon affixed to an exterior surface of the catheter, the balloon usable as a pressure sensor, and
      a balloon inflation lumen extending through the catheter in communication with the interior of the balloon through at least one aperture extending through the catheter;
   a stylet assembly, which can be removed from and inserted into the open end of the catheter, the assembly comprising
      a stylet for providing appropriate rigidity to the catheter to aid insertion into the esophagus, and
      a port for removably mounting a pressure transducer; and
   a pressure transducer, which can be removed from and inserted into the open end of the catheter, and which can be removed from and inserted into the port of the stylet assembly;
   wherein the stylet assembly further includes a coupler and a closure sealing an end of the coupler, and the stylet has an end affixed to a portion of the closure.

2. The esophageal catheter system according to claim 1, wherein the coupler includes the port for mounting the pressure transducer.

3. A stylet assembly for an esophageal catheter device having a balloon affixed to an exterior surface of the catheter, the balloon useable as a pressure sensor; the stylet assembly comprising:

a coupler;

a stylet having an end affixed to the coupler; and a port extending from the coupler for removably mounting a pressure transducer, wherein the stylet assembly further includes a closure sealing an end of the coupler, and the stylet has an end affixed to a portion of the closure.

4. A method for intra-thoracic pressure monitoring, the method comprising the steps of:

providing an esophageal catheter device including a catheter, a balloon affixed to an exterior surface of the catheter, the balloon useable as a pressure sensor, a balloon inflation lumen extending through the catheter in communication with the interior of the balloon through at least one aperture extending through the catheter, and a stylet assembly including a stylet for providing appropriate rigidity to the catheter to aid insertion in the esophagus and a port for removably mounting a pressure transducer;

mounting a pressure transducer to the port of the stylet assembly;

inserting the catheter device into an esophagus;

adding an amount of air to the sensor balloon;

positioning the sensor balloon of the catheter device in a desired location in the esophagus using pressure information obtained through the sensor balloon, the stylet assembly and pressure transducer working in concert, further comprising the steps of:

removing the pressure transducer from the port;

removing the stylet assembly from the open end of the catheter;

mounting the pressure transducer to the open end of the catheter; and monitoring esophageal pressure using pressure information obtained through the sensor balloon and the pressure transducer working in concert.

5. An esophageal catheter system comprising:

a catheter including:

an open end, for removably mounting one of a pressure transducer and a stylet assembly;

a closed end;

a balloon affixed to an exterior surface of the catheter, the balloon usable as a pressure sensor; and a balloon inflation lumen extending through the catheter in communication with the interior of the balloon through at least one aperture extending through the catheter;

a stylet assembly, which can be removed from and inserted into the open end of the catheter, the assembly comprising a stylet for providing appropriate rigidity to the catheter to aid insertion into the esophagus and a port for removably mounting the pressure transducer; and a pressure transducer, which can be removed from and inserted into the open end of the catheter, and which can be removed from and inserted into the port of the stylet assembly.

6. A method for intra-thoracic pressure monitoring, the method comprising the steps of:

providing an esophageal catheter system, the system comprising:

a catheter including an open end for removably mounting one of a pressure transducer and a stylet assembly, a balloon affixed to an exterior surface of the catheter and usable as a pressure sensor, a balloon inflation lumen extending through the catheter in communication with the interior of the balloon through at least one aperture extending through the catheter;

a stylet assembly, which can be removed from and replaced into the open end of the catheter, including a stylet for providing appropriate rigidity to the catheter to aid insertion in the esophagus and a port for removably mounting a pressure transducer; and a pressure transducer, which can be removed from and replaced into the open end of the catheter and which can be removed from and replaced into the port of the stylet assembly;

mounting the pressure transducer to the port of the stylet assembly;

inserting the catheter into an esophagus;

adding an amount of air to the balloon;

positioning the balloon of the catheter device in a desired location in the esophagus using pressure information obtaining through the balloon, the stylet assembly, and the pressure transducer working in concert.

* * * * *